United States Patent [19]

Starck et al.

[11] Patent Number: 4,671,072
[45] Date of Patent: Jun. 9, 1987

[54] SENSOR FOR DETECTING FROST DEPOSITS

[75] Inventors: Roland Starck, Rülzheim; Hanno Roller, Kandel, both of Fed. Rep. of Germany

[73] Assignee: Fritz Eichenauer GmbH & Co. KG, Kandel/Pfalz, Fed. Rep. of Germany

[21] Appl. No.: 804,603

[22] Filed: Dec. 4, 1985

[30] Foreign Application Priority Data

Dec. 4, 1984 [DE] Fed. Rep. of Germany ....... 3444171

[51] Int. Cl.$^4$ .............................................. F25D 21/02
[52] U.S. Cl. ..................................................... 62/140
[58] Field of Search ........................ 62/140, 156, 128; 340/580, 581; 324/65 R

[56] References Cited

U.S. PATENT DOCUMENTS

| 3,464,224 | 9/1969 | Swanson | 62/140 X |
| 3,899,895 | 8/1975 | Blanton et al. | 62/155 |
| 4,037,427 | 7/1977 | Kramer | 62/140 X |

Primary Examiner—Harry Tanner
Attorney, Agent, or Firm—Antonelli, Terry & Wands

[57] ABSTRACT

A sensor (1) for detecting frost deposits, particularly on evaporators of refrigeration plants or the like is proposed, in which between the spaced heat source (3) and heat sensor (4) is provided a thermal connection (2) made from a material, whose thermal conductivity coefficient is of the same order of magnitude as that of frost.

13 Claims, 6 Drawing Figures

SENSOR FOR DETECTING FROST DEPOSITS

BACKGROUND OF THE INVENTION

The present invention relates to a sensor for detecting frost deposits, particularly on evaporators in refrigeration plants and the like.

In refrigeration plants, such as cold stores and the like as a result of the cooling, in the case of supersaturated steam in the cooling chamber sublimation of the water vapor takes place on the cold fins or ribs or gills of the evaporator, so that frost is formed thereon. In the case of frost formation, part of the heat necessary for evaporating the cooling fluid in the evaporator does not come from the environment of the fins, so that they are further cooled, i.e. their temperature is decreased and instead use is made of the solidification or sublimation heat given off during frost formation. In the case of frost formation, there is also an increase of the fixed surface at which sublimation of the water vapour can take place. There is an overall decrease in the efficiency of the refrigeration plant, so that finally it is necessary to defrost the frost formed on the evaporator which once again calls for an energy supply. Defrosting takes place by incorporated electrical tubular heaters, which also pass through the fins, e.g. between the cold guide pipes passing through the evaporator fins. These electrical tubular heaters are called defrosting heaters. As such defrosting processes must be completed within a short time, because only the frost on the evaporator fins is to be removed by the heat supply, whereas, the cooling chamber must not be heated, a relatively large electrical capacity must be installed.

At present, evaporator defrosting takes place in different ways. Usually defrosting takes place by time synchronization, i.e. a time switch is provided, which switches in the defrosting plant at preselected time intervals, so that the frost is removed from the evaporator fins. With this time switching method, it is not possible to take account of the thickness of the frost or ice deposit, i.e. it is not possible in the optimum manner to defrost a frost layer of a certain, not excessive thickness and instead defrosting either takes place too early when there is still no frost deposit, or too late when the evaporator is already significantly frosted up. Attempts have been made to improve this in that switching in is not time-controlled and instead takes place via thermistors (U.S. Pat. No. 4,305,259). However, here again the heating period remains fixed. Due to its limited thermal conductivity coefficient, it is not possible to determine frost formation with its low density.

Another method takes account of the fact that the through-flow of air decreases with increasing frost deposits on the evaporator fins. Thus, the differential pressure is determined by measurement before and after evaporation. However, faulty switching can be caused by contamination and it is not always adequately accurately possible to detect the frost thickness.

In addition, a photo-optical method is known, in which a light beam is directed onto a receiver, so that when the light beam is interrupted by frost formation a signal is transmitted, which switches on the defrosting heater. Here again faults can occur due to contamination, as well as frost and ice formation on the transmitter and receiver, so that the defrosting plant is almost permanently switched on, although this is not required by the actual frost formation on the fins. Thermostatic control is also known, but is not suitable for detecting frost formation. Another measuring principle based on conductivity changes provides electrodes as test probes. Snow or ice or a medium arranged in a casing is initially melted and liquid between the electrodes once again switches on a defrosting plant (DE-OS Nos. 21 51 876, 31 09 366 and DE-AS No. 25 14 489). A method in which the conductivity between adjacent electrodes is measured directly without heating is based on the same principle (DE-OS No. 33 10 327). In addition, DE-OS No. 21 04 302 discloses producing heat by current, via a metal part acting as an electrical resistor, and to the metal part are soldered constant thermocouple wires to constitute a thermocouple, which through delays in the heating of the metal part can establish ice formation thereon.

In the known methods, unnecessary switch on/off signals for the defrosting heater are transmitted at the incorrect time, so that excessive energy and consequently great expense are expended.

The problem of the invention is to provide a sensor which, while avoiding the aforementioned disadvantages, very accurately detects frost formation and as a function thereof supplies a signal for switching on the defrosting plant as a function of the desired setting quantity.

According to the invention the above problem is solved with a sensor of the aforementioned type in that between a heat source and a heat sensor, which are spaced from one another, is provided a thermal connection of a material, whose thermal conductivity coefficient is of the same order of magnitude as the thermal conductivity coefficient of frost. Although the means according to the invention is particularly intended for detecting frost formation between the evaporator fins of a refrigeration plant, it can also be used for detecting snow and ice at switch points, in gutters and the like.

The invention is based on the fact that the heat produced by the heat source passes to the heat sensor, where it is detected. It is based on the idea that through frost formation an adequate heat proportion is removed from the aforementioned heat flow and is of the same order of magnitude as the heat quantity passing from the heat source to the heat sensor, so that much less heat passes to the latter than when there is no frost and the difference in the heat quantity in the absence of frost and in the presence of frost is of the same order of magnitude as the absolute heat quantity. It is important in this connection that the thermal conductivity coefficient of the material connecting the heat source and the heat sensor is of the same order of magnitude as the thermal conductivity coefficient of frost. If this connecting material has a much higher thermal conductivity coefficient, this would mean that even in the case of frost formation which, due to the "porosity" of frost has a very low thermal conductivity coefficient, virtually no heat would be removed and instead most of the heat produced would pass from the heat source to the sensor and the removed heat quantity, which is e.g. in the permille or lower percent range of the heat passing to the sensor and consequently within the error limit, e.g. through different cooling temperatures, electronic faults, etc. so that no usable signal is produced, i.e. despite frost formation the heat sensor would not transmit a signal for switching on the defrosting heater.

However, as a result of the sensor construction according to the invention, it is possible to obtain a usable electrical signal for switching the defrosting plant in a sufficiently accurate manner as a result of the adequately different heat flow and the resulting differing influencing of the sensor in the case of frost and ice formation.

According to a preferred development, the heat source and heat sensor are arranged in a common casing aud the latter forms the connection with a thermal conductivity coefficient of the same order of magnitude as that of frost. Materials for the same can be selected from the relevant tables (e.g. according to Dubbel) due to the conditions involved with the solution according to the invention. A preferred sleeve or casing material is e.g. silicone rubber provided with additives or admixtures, such as carbon black, because this material has the necessary stability and elasticity, apart from the thermal conductivity coefficient which can be set through its density and in particular the admixture of carbon black.

In a preferred manner, the heat source has a PTC resistor.

Thus, even in the case of varying environmental conditions, the heat quantity reaching the heat sensor fluctuates very little, assuming the same degree of frosting. In this case, the sensor can be constructed on the basis of a sleeve-like resistant heater according to German Pat. No. 29 48 592 and in addition to the PTC resistor as the heat source in the sleeve is provided a heat sensor and it must be ensured that if there is contacting of the PTC resistor via metallic contact plates, their dimensions must be adapted to those of the PTC resistor and must never extend up to the heat sensor, so that no heat bridge with a high thermal conductivity coefficient is formed.

According to a further development, the heat sensor is constructed as a NTC-resistor, or is constructed as a semiconductor and in particular silicon heat sensor, which has a good, accurate measuring range between $-50°$ C. and $0°$ C.

Further advantages and features of the invention can be gathered from the claims and the following description of an embodiment of the invention when taken in connection with the accompanying drawings.

DETAILED DESCRIPTION

Figure 1:
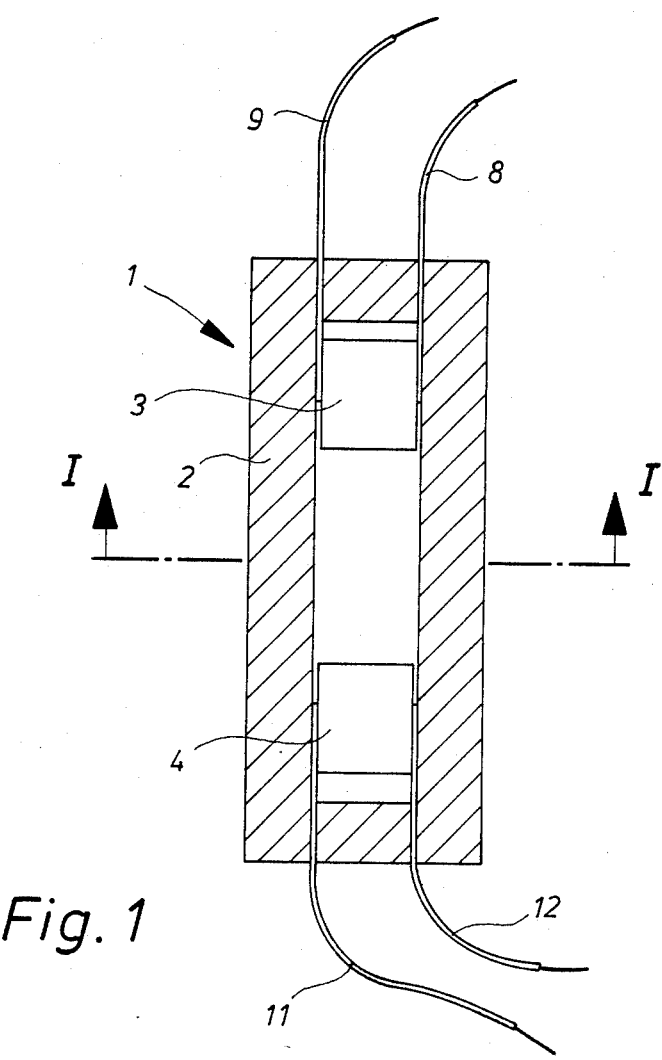
FIG. 1 is a longitudinal section through a sensor according to the invention.
Figure 2:
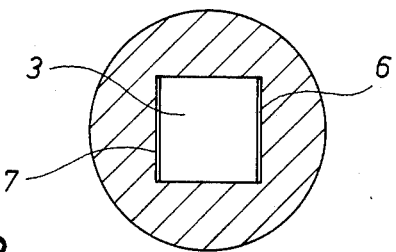
FIG. 2 is a cross-section through the sensor of FIG. 1 taken along the line I—I.

The sensor 1 according to the invention has an external sleeve or casing 2, which is of a cylindrical or parallelpipedic configuration and is made from a material with a thermal conductivity coefficient of the same order of magnitude as that of frost, $\lambda = 0.09$ W/mK (the thermal conductivity coefficient of snow is highly dependent on its density and ranges from 0.05 W/mK at a density of 100 Kg/m$^3$ to e.g. 0.52 W/mK at a density of 400 Kg/m$^3$, frost corresponding to light snow with a density of approximately 100 to 150 Kg/m$^3$). The actual sleeve dimensions are not critical. Generally such sleeves have a length of 5 to 8 cm, a diameter of 0.05 to 1.5 cm and wall thickness of 0.2 to 0.5 cm. Suitable sleeve materials can be gathered from the thermal conductivity coefficient tables of the standard literature. A preferred material for reduciug the thermal conductivity is silicone rubber mixed with carbon black or a corresponding plastic which, apart from giving a suitable thermal conductivity, also ensures the necessary high mechanical strength. The thermal conductivity coefficient of sleeve 2 can also be set in an appropriate manner by a suitable proportion of MgO particles in silicone rubber or the like. The sleeve has a cavity in which are arranged in spaced manner a heater 3 and a sensor 4. In the represented embodiment the space between heater 3 and sensor 4 is empty or contains air. However it could also be filled with the sleeve material. The heater is preferably a self-stabilizing element with a positive temperature coefficient, but can also be a fixed resistor. As a PTC resistor, heater 3 has metal contacting in its surfaces 6 and 7 and from this leads 8, 9 pass out of sleeve 2 and are passed to a voltage source.

The sensor can e.g. be a NTC resistor, whose resistance drops with the temperature. However, it is also possible to use other heat sensors, such as thermocouples and in particular silicon heat sensors. Sensor 4 gives a signal varying with the temperature via leads 11 12, which is then used for switching the defrosting units.

Figure 3:
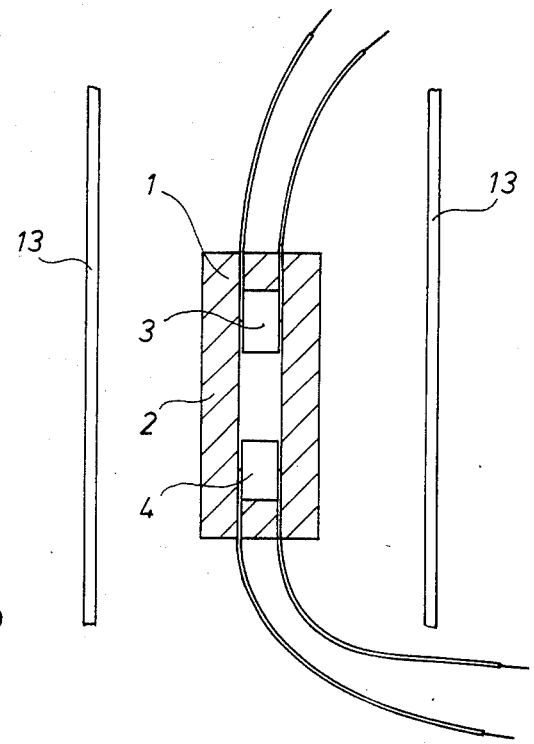
FIG. 3 is a partial cross-sectional view of the FIG. 1 disposed between two fins of an evaporator of a refrigeration plant, with the latter being in an unfrosted state.
Figure 4:
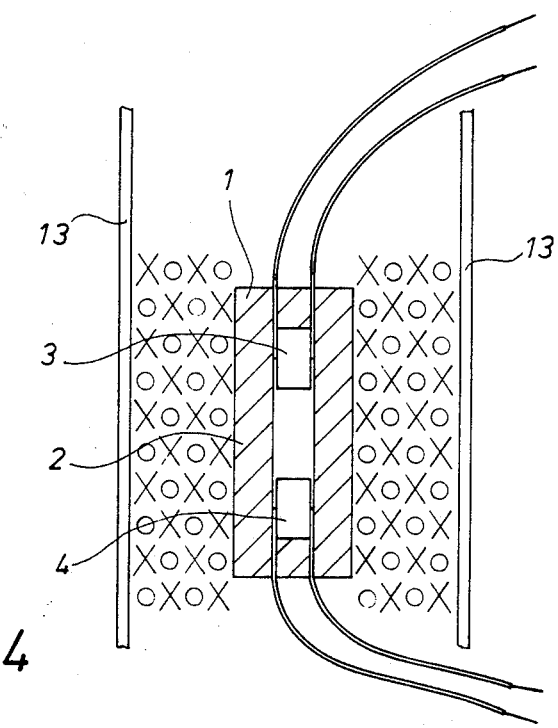
FIG. 4 is a partial cross-sectional view of the sensor of FIG. 3, in which frost has formed between sensor and fins of the evaporator of the refrigeration plant.

The arrangement of a heat sensor according to the invention in an evaporator of a refrigeration plant is shown in FIGS. 3 and 4. Such an evaporator has ribs or fins, which are traversed by cooling fluid lines, in which the cooling fluid is evaporated by expansion and removes heat from the environment for evaporation via the fins, so that the environment is cooled. On cooling, as a result of the supersaturated steam, the latter can be sublimated on the fins and consequently deposited as frost (FIG. 4). Frost formation is disadvantageous, because as a result thereof the cooling capacity is not used for cooling, i.e. reducing the temperature, but instead largely for forming frost and through the increase in the surface due to the frost, further frost can be deposited and the condensation losses rise. Frost formation must therefore be prevented, or at least eliminated at an early stage.

Figure 5:
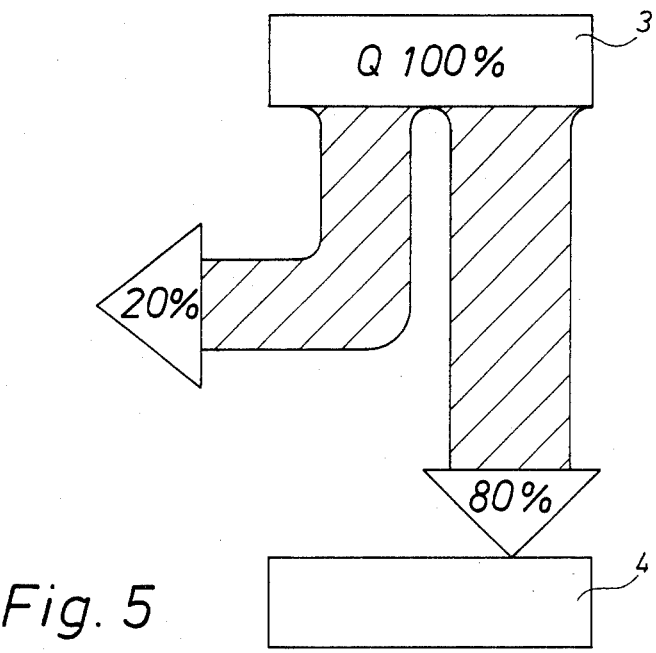
FIG. 5 is a diagramatic view illustrating the heat flow in the state of FIG. 3.
Figure 6:
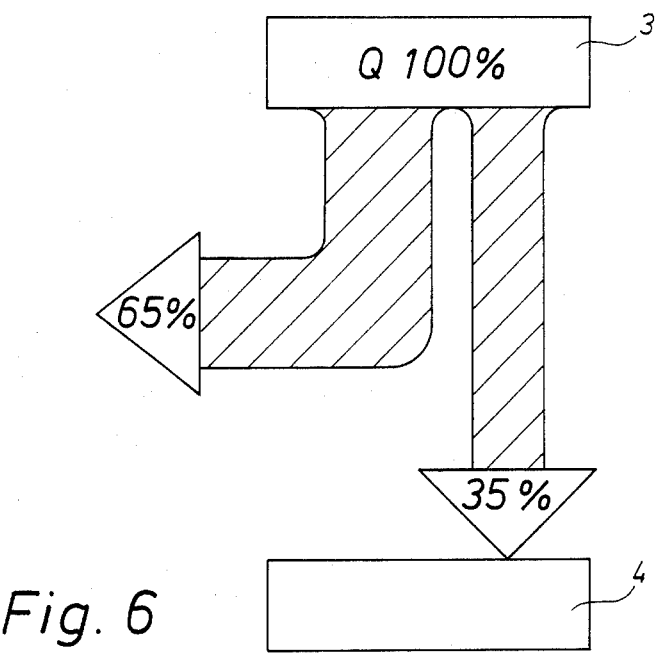
FIG. 6 is a diagrammatic view illustrating the heat flow in the state of FIG. 4.

If no frost has formed (FIG. 3), part of the heat produced in heater 3 flows via sleeve 2 to sensor 4, while a further smaller portion, which is fundamentally of the same order of magnitude, is given off via the outer sleeve wall, as shown in FIG. 5. The percentages given are merely illustrative hypothetical values or constitute rough estimates. If frost now forms between the fins 13 and comes into contact with sensor 4, due to the fact that the thermal conductivity coefficient of the material sleeve 2 is of the same order of magnitude as that of frost (and not significantly higher), a greater quantity of the heat produced by heater 3 can be supplied to the frost (due to its higher thermal conductivity compared with air, i.e. approximately 0.02 W/mK at $-20°$ C.) and contributes to a very small temperature increase due to the mass of the frost in which it is distributed by dissipation and is possibly used there as melting heat, or can be more easily given off to the environment by the surface increased by the frost. These conditions are shown in FIG. 4. As the thermal conductivity coefficient of the sleeve material and the frost deposit are roughly the same, there is a change to the heat absorbed by the heat sensor or which is in particular of the same order of magnitude as the absolutely absorbed heat and can consequently be easily measured and/or further processed for heating heating elements for defrosting the cooling fins. The signal cannot be influenced particularly by environmental influences, fault sources, etc., such as e.g. through differing cooling capacity of the refrigeration unit, etc. If the thermal conductivity coefficient of the material connecting the heater 3 and the sensor is much higher than that of frost, then the heat flow without frost deposit would be almost 100% and the modification to the heat flow due to frost deposits would be in the permille or lower percent range and, consequently, 1 to 2 orders of magnitude below that of the absolute heart flow, so that no usable signal would be obtained. Thus, sleeves or connecting parts between the heater and the sensor must not be made from metal.

We claim:

1. A sensor comprising means for detecting frost deposits on evaporators of refrigeration plants including a heat source means, heat sensor means spaced from said heat source means, and means for forming a thermal connection between said heat source means and said heat sensor means, and wherein said means-for forming a thermal connection is made from a material having a thermal conductivity coefficient of the same magnitude as that of frost.

2. Sensor according to claim 1, wherein said means for forming the thermal connection includes a common casing means for accommodating the heat source means and heat sensor means are arranged in a common casing.

3. Sensor according to claim 2, wherein the casing means is cylindrical.

4. Sensor according to claim 2, wherein the casing means is parallepipedic.

5. Sensor according to one of claims 1 or 2, wherein the heat source means includes a PTC resistor.

6. Sensor according to claim 5, wherein the heat source means includes an electrical heater with a fixed resistor.

7. Sensor according to claim 5, wherein the heat sensor means is constructed as a NTC resistor.

8. Sensor according to claim 5, wherein the heat sensor means includes a thermocouple.

9. Sensor according to claim 5, wherein the heat sensor means includes a semiconductor heat sensor.

10. Sensor according to one of claims 1 or 2, wherein the heat source means includes an electrical heater with a fixed resistor.

11. Sensor according to one of claims 1 or 2 wherein the heat sensor means is constructed as a NTC resistor.

12. Sensor according to one of claims 1 or 2 wherein the heat sensor means includes a thermocouple.

13. Sensor according to one of claims 1 or 2 wherein the heat sensor means includes a semiconductor heat sensor.

* * * * *